(12) United States Patent
Delfort et al.

(10) Patent No.: US 10,967,325 B2
(45) Date of Patent: Apr. 6, 2021

(54) ABSORBENT SOLUTION BASED ON HYDROXYL DERIVATIVES OF 1,6-HEXANEDIAMINE AND METHOD FOR ELIMINATING ACID COMPOUNDS FROM A GASEOUS EFFLUENT

(71) Applicant: IFP Energies nouvelles, Rueil-Malmaison (FR)

(72) Inventors: Bruno Delfort, Paris (FR); Julien Grandjean, Lyons (FR); Thierry Huard, Saint Symphorien d'Ozon (FR); Laetitia Giraudon, Saint Michel sur Rhone (FR); Catherine Lefebvre, Le Pecq (FR); Aurelie Wender, Rueil-Malmaison (FR); Armelle Nigon, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 302 days.

(21) Appl. No.: 16/062,820

(22) PCT Filed: Dec. 13, 2016

(86) PCT No.: PCT/EP2016/080827
§ 371 (c)(1),
(2) Date: Jun. 15, 2018

(87) PCT Pub. No.: WO2017/102746
PCT Pub. Date: Jun. 22, 2017

(65) Prior Publication Data
US 2020/0254380 A1    Aug. 13, 2020

(30) Foreign Application Priority Data
Dec. 17, 2015 (FR) ........................ 1562670

(51) Int. Cl.
*B01D 53/14* (2006.01)
*C07C 215/18* (2006.01)
*C10L 3/10* (2006.01)

(52) U.S. Cl.
CPC ..... *B01D 53/1493* (2013.01); *B01D 53/1425* (2013.01); *B01D 53/1468* (2013.01);
(Continued)

(58) Field of Classification Search
USPC .......................................................... 423/228
See application file for complete search history.

(56) References Cited

U.S. PATENT DOCUMENTS

| 6,596,663 B1 | 7/2003 | Tamano |
| 8,845,787 B2 | 9/2014 | Jacquin |

(Continued)

FOREIGN PATENT DOCUMENTS

FR    2934172 A1    1/2010

OTHER PUBLICATIONS

International Search Report PCT/EP2016/080827 dated Mar. 21, 2017.

*Primary Examiner* — Anita Nassiri-Motlagh
(74) *Attorney, Agent, or Firm* — Millen White Zelano and Branigan, PC; John Sopp (57) ABSTRACT

The invention relates to an absorbent solution and to a method using this solution for removing acid compounds contained in a gaseous effluent, comprising water and at least one diamine with general formula (I) as follows:

(Continued)

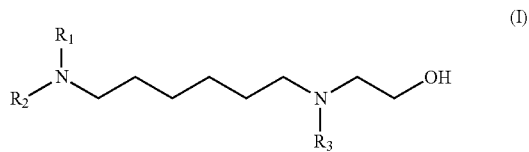

wherein:
radicals $R_1$, $R_2$, $R_3$ are each selected indiscriminately among a methyl radical and a hydroxyethyl radical, and
at least one radical among $R_1$, $R_2$, $R_3$ is a methyl radical.

15 Claims, 5 Drawing Sheets

(52) U.S. Cl.
CPC ............ *C07C 215/18* (2013.01); *C10L 3/103* (2013.01); *B01D 2252/2041* (2013.01); *B01D 2252/20431* (2013.01); *B01D 2252/20484* (2013.01); *B01D 2252/20489* (2013.01); *B01D 2252/504* (2013.01); *C10L 2290/542* (2013.01)

(56) References Cited

U.S. PATENT DOCUMENTS

| | | |
|---|---|---|
| 8,877,825 B2 | 11/2014 | Kometani |
| 2003/0144371 A1 | 7/2003 | Kometani |

ABSORBENT SOLUTION BASED ON HYDROXYL DERIVATIVES OF 1,6-HEXANEDIAMINE AND METHOD FOR ELIMINATING ACID COMPOUNDS FROM A GASEOUS EFFLUENT

FIELD OF THE INVENTION

The present invention relates to the field of gaseous effluent deacidizing methods. The invention is advantageously applied to the treatment of gas of industrial origin and of natural gas.

BACKGROUND OF THE INVENTION

Gas deacidizing methods using aqueous amine solutions for removing acid compounds present in a gas, notably carbon dioxide ($CO_2$), hydrogen sulfide ($H_2S$), carbon oxysulfide (COS), carbon disulfide ($CS_2$), sulfur dioxide ($SO_2$) and mercaptans (RSH) such as methylmercaptan ($CH_3SH$), ethylmercaptan ($CH_3CH_2SH$) and propylmercaptan ($CH_3CH_2CH_2SH$), are commonly used. The gas is deacidized by being contacted with the absorbent solution, then the absorbent solution is thermally regenerated.

These acid gas deacidizing methods are also commonly known as "solvent scrubbing", using a solvent referred to as "chemical", as opposed to the use of a solvent referred to as "physical" for absorption that is not based on chemical reactions.

A chemical solvent corresponds to an aqueous solution comprising a reactant that reacts selectively with the acid compounds ($H_2S$, $CO_2$, COS, $CS_2$, etc.) present in the treated gas so as to form salts, without reacting with the other non-acid compounds in the gas. After contacting with the solvent, the treated gas is depleted in acid compounds that are selectively transferred as salts into the solvent. The chemical reactions are reversible, which allows the acid compound-laden solvent to be subsequently deacidized, for example under the action of heat, so as to release on the one hand the acid compounds in form of gas that can then be stored, converted or used for various applications, and on the other hand to regenerate the solvent that goes back to its initial state and can thus be used again for a new reaction step with the acid gas to be treated. The reaction step of the solvent with the acid gas is commonly referred to as absorption step, and the step where the solvent is deacidized is referred to as solvent regeneration step.

In general, the performances of the separation of acid compounds from the gas in this context mainly depend on the nature of the reversible reaction selected. Conventional acid gas deacidizing methods are generally referred to as "amine methods", i.e. based on the reactions of the acid compounds with amines in solution. These reactions are part of the overall framework of acid-base reactions. $H_2S$, $CO_2$ or COS are for example acid compounds, notably in the presence of water, whereas amines are basic compounds. The reaction mechanisms and the nature of the salts obtained generally depend on the structure of the amines used.

For example, document U.S. Pat. No. 6,852,144 describes a method of removing acid compounds from hydrocarbons using a water-N-methyldiethanolamine or water-triethanolamine absorbent solution with a high proportion of at least one compound belonging to the following group: piperazine and/or methylpiperazine and/or morpholine.

The performances of acid gas deacidizing methods using amine scrubbing directly depend on the nature of the amine (s) present in the solvent. These amines can be primary, secondary or tertiary. They can have one or more equivalent or different amine functions per molecule.

In order to improve the performances of deacidizing methods, increasingly efficient amines are continuously sought.

One limitation of the absorbent solutions commonly used in deacidizing applications is insufficient $H_2S$ absorption selectivity over $CO_2$. Indeed, in some natural gas deacidizing cases, selective $H_2S$ removal is sought by limiting to the maximum $CO_2$ absorption. This constraint is particularly important for gases to be treated already having a $CO_2$ content that is less than or equal to the desired specification. A maximum $H_2S$ absorption capacity is then sought with maximum $H_2S$ absorption selectivity over $CO_2$. This selectivity allows to maximize the amount of treated gas and to recover an acid gas at the regenerator outlet having the highest $H_2S$ concentration possible, which limits the size of the sulfur chain units downstream from the treatment and guarantees better operation. In some cases, an $H_2S$ enrichment unit is necessary for concentrating the acid gas in $H_2S$. In this case, the most selective amine is also sought. Tertiary amines such as N-methyldiethanolamine or hindered secondary amines exhibiting slow reaction kinetics with $CO_2$ are commonly used, but they have limited selectivities at high $H_2S$ loadings.

It is well known to the person skilled in the art that tertiary amines or secondary amines with severe steric hindrance have slower $CO_2$ capture kinetics than less hindered primary or secondary amines. On the other hand, tertiary or secondary amines with severe steric hindrance have instantaneous $H_2S$ capture kinetics, which allows to achieve selective $H_2S$ removal based on distinct kinetic performances.

Various documents propose using hindered tertiary or secondary amines, in particular hindered tertiary or secondary diamines, in solution for deacidizing acid gases.

Among the applications of tertiary or secondary amines with severe steric hindrance, patent U.S. Pat. No. 4,405,582 describes a method for selective absorption of sulfur-containing gases with an absorbent containing a diaminoether at least one amine function of which is tertiary and whose other amine function is tertiary or secondary with severe steric hindrance, the nitrogen atom being in the latter case linked to either at least one tertiary carbon or to two secondary carbon atoms. The two amine functions and the carbons of the main chain can be substituted by alkyl or hydroxyalkyl radicals.

U.S. Pat. No. 4,405,583 also describes a method for selective removal of $H_2S$ in gases containing $H_2S$ and $CO_2$ with an absorbent containing a diaminoether whose two secondary amine functions exhibit severe steric hindrance as defined above. The substituents of the amine functions and of the carbons of the main chain can be substituted by alkyl and hydroxyalkyl radicals.

Another limitation of the absorbent solutions commonly used in total deacidizing applications is too slow $CO_2$ or COS capture kinetics. In cases where the desired $CO_2$ or COS specifications level is very high, the fastest possible reaction kinetics is sought so as to reduce the height of the absorption column. Indeed, this equipment under pressure represents a significant part of the investment costs of the process.

Whether seeking maximum $CO_2$ and COS capture kinetics in a total deacidizing application or minimum $CO_2$ capture kinetics in a selective application, it is always desirable to use an absorbent solution having the highest cyclic capacity possible. This cyclic capacity, denoted by $\Delta\alpha$, corresponds to the loading difference ($\alpha$ designates the number of moles of absorbed acid compounds $n_{acid\ gas}$ per kilogram of absorbent solution) between the absorbent solution discharged from the bottom of the absorption column and the absorbent solution fed to said column. Indeed, the higher the cyclic capacity of the absorbent solution, the lower the absorbent solution flow rate required for deacidizing the gas to be treated. In gas treatment methods, reduction of the absorbent solution flow rate also has a great impact on the reduction of investments, notably as regards absorption column sizing.

Another essential aspect of gas or industrial fumes treatment operations using a solvent remains the regeneration of the separation agent. Regeneration through expansion and/or distillation and/or entrainment by a vaporized gas referred to as "stripping gas" is generally considered, depending on the absorption type (physical and/or chemical). The energy consumption required for solvent regeneration can be very high, which is in particular the case when the acid gas partial pressure is low, and it can represent a considerable operating cost for the $CO_2$ capture process.

It is well known to the person skilled in the art that the energy required for regeneration by distillation of an amine solution can be divided into three different items: the energy required for heating the absorbent solution between the top and the bottom of the regenerator, the energy required for lowering the acid gas partial pressure in the regenerator by vaporization of a stripping gas, and finally the energy required for breaking the chemical bond between the amine and the $CO_2$.

These first two items are proportional to the absorbent solution flows to be circulated in the plant in order to achieve a given specification. To decrease the energy consumption linked with the regeneration of the solvent, the cyclic capacity of the solvent is therefore once again preferably maximized. Indeed, the higher the cyclic capacity of the absorbent solution, the lower the absorbent solution flow rate required for deacidizing the gas to be treated.

There is therefore a need, in the field of gas deacidizing, for compounds that are good candidates for acid compounds removal from a gaseous effluent, notably, but not exclusively, selective removal of $H_2S$ over $CO_2$, and that allow operation at lower operating costs (including the regeneration energy) and investment costs (including the cost of the absorption column).

DESCRIPTION OF THE INVENTION

The inventors have found that tertiary or secondary diamines with severe steric hindrance are not equivalent in terms of performance for use in absorbent solution formulations for acid gas treatment in an industrial process.

The object of the present invention is the use, in the field of gas deacidizing, of diamines of general formula (I) given below in aqueous solution, which diamines are hydroxyl derivatives of 1,6-hexanediamine.

The inventors have found that using these compounds allows to obtain good performances in terms of cyclic acid gas absorption capacity and of absorption selectivity towards $H_2S$, notably a higher absorption selectivity towards $H_2S$ than reference amines such as N-methyldiethanolamine (MDEA) for an equivalent or higher cyclic acid gas absorption capacity.

SUMMARY OF THE INVENTION

According to a first aspect, the invention relates to an absorbent solution for removing acid compounds contained in a gaseous effluent, comprising:

water,
at least one nitrogen compound with general formula (I) as follows:

(I)

wherein:
radicals $R_1$, $R_2$, $R_3$ are each selected indiscriminately among a methyl radical and a hydroxyethyl radical, and at least one radical among $R_1$, $R_2$, $R_3$ is a methyl radical.

According to the invention, the nitrogen compound can be selected from the following compounds:

N,N,N'-trimethyl-N'-(2-hydroxyethyl)-1,6-hexanediamine with formula ($I_1$) as follows:

($I_1$)

N,N'-dimethyl-N,N'-di(2-hydroxyethyl)-1,6-hexanediamine with formula ($I_2$):

($I_2$)

N,N-dimethyl-N',N'-di(2-hydroxyethyl)-1,6-hexanediamine with formula ($I_3$):

($I_3$)

N-methyl-N,N',N'-tri(2-hydroxyethyl)-1,6-hexanediamine with formula ($I_4$):

($I_4$)

Preferably, the nitrogen compound is N,N,N'-trimethyl-N'-(2-hydroxyethyl)-1,6-hexanediamine with formula ($I_1$) or N,N'-dimethyl-N,N'-di(2-hydroxyethyl)-1,6-hexane-diamine with formula ($I_2$).

According to the invention, the absorbent solution can comprise between 5 wt. % and 95 wt. % of nitrogen compound, preferably between 10 wt. % and 90 wt. % of nitrogen compound, and between 5 wt. % and 95 wt. % of water, preferably between 10 wt. % and 90 wt. % of water.

The solution advantageously comprises between 20 wt. % and 50 wt. % of said nitrogen compound, and between 50 wt. % and 80 wt. % of water.

Furthermore, the absorbent solution can comprise between 5 wt. % and 95 wt. % of at least one additional amine, said additional amine being either a tertiary amine or a secondary amine having two secondary carbons at nitrogen alpha position or at least one tertiary carbon at nitrogen alpha position.

The additional amine can be a tertiary amine selected from the group made up of:
N-methyldiethanolamine,
triethanolamine,
diethylmonoethanolamine,
dimethylmonoethanolamine, and
ethyldiethanolamine.

The absorbent solution can also comprise a non-zero amount, less than 30 wt. %, of at least one primary or secondary amine.

The primary or secondary amine can be selected from the group made up of:
monoethanolamine,
diethanolamine,
N-butylethanolamine,
aminoethylethanolamine,
diglycolamine,
piperazine,
1-methylpiperazine,
2-methylpiperazine,
homopiperazine,
N-(2-hydroxyethyl)piperazine,
N-(2-aminoethyl)piperazine,
morpholine,
3-(methylamino)propylamine,
1,6-hexanediamine,
N,N-dimethyl-1,6-hexanediamine,
N,N'-dimethyl-1,6-hexanediamine,
N-methyl-1,6-hexanediamine, and
N,N',N'-trimethyl-1,6-hexanediamine.

The absorbent solution can furthermore comprise at least one physical solvent selected from the group made up of methanol, ethanol, 2-ethoxyethanol, triethylene glycol dimethyl ether, tetraethylene glycol dimethyl ether, pentaethylene glycol dimethyl ether, hexaethylene glycol dimethyl ether, heptaethylene glycol dimethyl ether, octaethylene glycol dimethyl ether, diethylene glycol butoxyacetate, glycerol triacetate, sulfolane, N-methylpyrrolidone, N-methyl-morpholin-3-one, N,N-dimethyl-formamide, N-formylmorpholine, N,N-dimethylimidazolidin-2-one, N-methylimidazole, ethylene glycol, diethylene glycol, triethylene glycol, thiodiglycol, propylene carbonate and tributyl phosphate.

According to a second aspect, the invention relates to a method of removing acid compounds contained in a gaseous effluent wherein an acid compound absorption step is carried out by contacting the gaseous effluent with an absorbent solution according to the invention.

Preferably, the acid compound absorption step is carried out at a pressure ranging between 1 bar and 200 bar, and at a temperature ranging between 20° C. and 100° C.

Preferably, an absorbent solution laden with acid compounds is obtained after the absorption step and at least one step of regeneration of the acid compound-laden absorbent solution is performed at a pressure ranging between 1 bar and 10 bar, and at a temperature ranging between 100° C. and 180° C.

The gaseous effluent can be selected among natural gas, syngases, combustion fumes, refinery gas, acid gas from an amine plant, Claus tail gas, biomass fermentation gas, cement plant gas and incinerator fumes.

The method according to the invention can be implemented for selectively removing the $H_2S$ over the $CO_2$ from a gaseous effluent comprising $H_2S$ and $CO_2$.

BRIEF DESCRIPTION OF THE FIGURES

Other features and advantages of the invention will be clear from reading the description hereafter of embodiments given by way of non limitative example, with reference to the accompanying figures wherein.

In FIGS. 2 to 8, the abbreviation "cat" stands for catalyst and the arrows represent reaction steps. These are reaction schemes that do not comprise all of the components required for conducting the synthesis. Only the elements necessary for understanding the invention are shown.

DETAILED DESCRIPTION OF THE INVENTION

The present invention aims to remove acid compounds from a gaseous effluent using an aqueous solution whose composition is detailed hereafter.

Composition of the Absorbent Solution

The absorbent solution used for removing the acid compounds contained in a gaseous effluent comprises:
water,
at least one nitrogen compound with general formula (I) as follows:

(I)

wherein:
radicals $R_1$, $R_2$, $R_3$ are each selected indiscriminately among a methyl radical and a hydroxyethyl radical, and at least one radical among $R_1$, $R_2$, $R_3$ is a methyl radical.

Preferably, radicals $R_1$ and $R_3$ are methyl radicals and radical $R_2$ is a methyl or hydroxyethyl radical.

More preferably, radicals $R_1$ and $R_3$ are methyl radicals and radical $R_2$ is a hydroxyethyl radical.

The absorbent solution according to the invention can advantageously comprise at least one of the following compounds:

N,N,N'-trimethyl-N'-(2-hydroxyethyl)-1,6-hexanediamine with formula (I₁) as follows:

N,N'-dimethyl-N,N'-di(2-hydroxyethyl)-1,6-hexanediamine with formula (I₂) as follows:

N,N-dimethyl-N',N'-di(2-hydroxyethyl)-1,6-hexanediamine with formula (I₃) as follows:

N-methyl-N,N',N'-tri(2-hydroxyethyl)-1,6-hexanediamine with formula (I₄) as follows:

The nitrogen compound of general formula (I) can be in variable concentration in the absorbent solution, ranging for example between 5 wt. % and 95 wt. %, preferably between 10 wt. % and 90 wt. %, more preferably between 20 wt. % and 50 wt. %, inclusive.

The absorbent solution can contain between 5 wt. % and 95 wt. % of water, preferably between 10 wt. % and 90 wt. %, more preferably between 50 wt. % and 80 wt. %, inclusive.

The sum of the mass fractions expressed in wt. % of the various compounds of the absorbent solution is 100 wt. % of the absorbent solution.

According to one embodiment, the absorbent solution can further contain at least one additional amine that is a tertiary amine, such as N-methyldiethanolamine, triethanolamine, diethylmonoethanolamine, dimethylmonoethanolamine or ethyl-diethanolamine, or a secondary amine with severe steric hindrance, this hindrance being defined by either the presence of two secondary carbons at nitrogen alpha position or at least one tertiary carbon at nitrogen alpha position. Said additional amine is understood to be any compound having at least one severely hindered tertiary or secondary amine function. The concentration of said severely hindered tertiary or secondary additional amine in the absorbent solution can range between 5 wt. % and 95 wt. %, preferably between 5 wt. % and 50 wt. %, more preferably between 5 wt. % and 30 wt. %.

According to an embodiment, the amines of general formula (I) can be formulated with one or more compounds containing at least one primary or secondary amine function. For example, the absorbent solution comprises a concentration of up to 30 wt. %, preferably below 15 wt. % and preferably below 10 wt. % of said compound containing at least one primary or secondary amine function. Preferably, the absorbent solution comprises at least 0.5 wt. % of said compound containing at least one primary or secondary amine function. Said compound allows to accelerate the absorption kinetics of the $CO_2$ and, in some cases, of the COS contained in the gas to be treated.

A non-exhaustive list of compounds containing at least one primary or secondary amine function that can go into the formulation is given below:
monoethanolamine,
diethanolamine,
N-butylethanolamine,
aminoethylethanolamine,
diglycolamine,
piperazine,
1-methylpiperazine,
2-methylpiperazine,
homopiperazine,
N-(2-hydroxyethyl)piperazine,
N-(2-aminoethyl)piperazine,
morpholine,
3-(metylamino)propylamine,
1,6-hexanediamine and all the diversely N-alkylated derivatives thereof such as, for example, N,N'-dimethyl-1,6-hexanediamine, N,N-dimethyl-1,6-hexanediamine, N-methyl-1,6-hexanediamine or N,N',N'-trimethyl-1,6-hexane-diamine.

According to the invention, the absorbent solution comprising a nitrogen compound of general formula (I) can contain a mixture of additional amines as defined above.

According to an embodiment, the absorbent solution can contain organic compounds non reactive towards the acid compounds (commonly referred to as "physical solvents"), which allow to increase the solubility of at least one or more acid compounds of the gaseous effluent. For example, the absorbent solution can comprise between 5 wt. % and 50 wt. % of physical solvent such as alcohols, ethers, ether alcohols, glycol and polyethylene glycol ethers, glycol thioethers, glycol and polyethylene glycol esters and alkoxyesters, glycerol esters, lactones, lactames, N-alkylated pyrrolidones, morpholine derivatives, morpholin-3-one, imidazoles and imidazolidinones, N-alkylated piperidones, cyclotetramethylenesulfones, N-alkylformamides, N-alkylacetamides, ether-ketones, alkyl carbonates or alkyl phosphates and derivatives thereof. By way of non limitative example, it can be methanol, ethanol, 2-ethoxyethanol, triethylene glycol dimethyl ether, tetraethylene glycol dimethyl ether, pentaethylene glycol dimethyl ether, hexaethylene glycol dimethyl ether, heptaethylene glycol dimethyl ether, octaethylene glycol dimethyl ether, diethylene glycol butoxyacetate, glycerol triacetate, sulfolane, N-methylpyrrolidone, N-methylmorpholin-3-one, N,N-dimethyl-formamide, N-formyl-morpholine, N,N-dimethyl-imidazolidin-2-one, N-methyl-imidazole, ethylene glycol, diethylene glycol, triethylene glycol, thiodiglycol, propylene carbonate, tributylphosphate.

Synthesis of the Nitrogen Compounds with the General Formula

The compounds with the general formula of the invention can be synthesized according to any method permitted by organic chemistry and notably by means of the following methods.

Method 1: Synthesis from 1,6-Hexanediamine

A first method consists of the succession of two reaction steps from 1,6-hexanediamine.

Figure 2A:
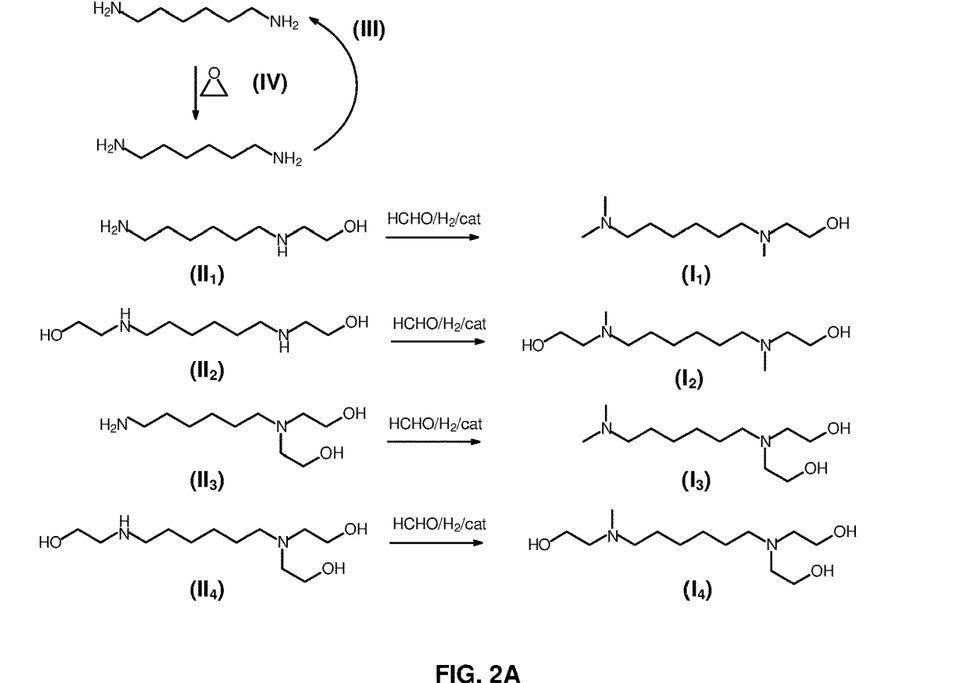
FIGS. 2A and 2B illustrate a synthesis method for compounds of general formula (I) from 1,6-hexanediamine according to two variants.

FIG. 2A illustrates the synthesis of at least one compound of general formula (I) from 1,6-hexanediamine, of formula (III).

The first step consists in reacting the 1,6-hexanediamine with ethylene oxide (formula IV) in suitable amount and conditions so as to obtain either a partly ethoxylated 1,6-hexanediamine such as N-(2-hydroxyethyl)-1,6-hexanediamine (formula $II_1$) or N-N'-di(2-hydroxyethyl)-1,6-hexanediamine (formula $II_2$) or N-N-di(2-hydroxyethyl)-1,6-hexanediamine (formula $II_3$) or N-N-N'-tri(2-hydroxyethyl)-1,6-hexanediamine (formula $II_4$), or a mixture of these molecules. These partly ethoxylated 1,6-hexanediamines of formula ($II_1$) to ($II_4$) are intermediate products in this synthesis mode.

The reaction conditions are suited in order not to obtain N,N,N',N'-tetra(2-hydroxyethyl)-1,6-hexanediamine and to minimize the amount of residual 1,6-hexanediamine. It is therefore advantageous to operate with a molar ratio of ethylene oxide to 1,6-hexanediamine not exceeding 3/1, preferably not exceeding 2.5/1. The selection of the molar ratio between the ethylene oxide and the 1,6-hexanediamine conditions the composition of the products obtained.

When residual 1,6-hexanediamine is present, it can be removed from the medium by distillation for example and optionally recycled.

When N,N,N',N'-tetra(2-hydroxyethyl)-1,6-hexanediamine is obtained, it can be removed from the medium by distillation for example.

When a mixture of intermediate compounds is obtained, it can be used as it is to carry out the second step or it can be subjected to separation, by distillation for example, in order to obtain one of the compounds of general formula (I) or a combination of these compounds (formulas $I_1$ to $I_4$) at the end of the second step.

The second step consists in the methylation of the primary or secondary amine functions of the intermediate products (of formulas $II_1$ to $II_4$) obtained in the first step in order to lead to N,N,N'-trimethyl-N'-(2-hydroxyethyl)-1,6-hexanediamine (formula $I_1$) and/or N,N'-dimethyl-N-N'-di(2-hydroxyethyl)-1,6-hexanediamine (formula $I_2$) and/or N,N-dimethyl-N'-N'-di(2-hydroxyethyl)-1,6-hexanediamine (formula $I_3$) and/or N-methyl-N-N'-N'-tri(2-hydroxyethyl)-1,6-hexanediamine (formula $I_4$).

Methylation of the amine functions can be achieved using any means known to the person skilled in the art, notably through the reaction of formaldehyde and hydrogen in the presence of a suitable catalyst (as shown in FIG. 2A) or for example the reaction of formaldehyde and formic acid according to the reaction known as Eschweiler-Clarke reaction.

Figure 2B:
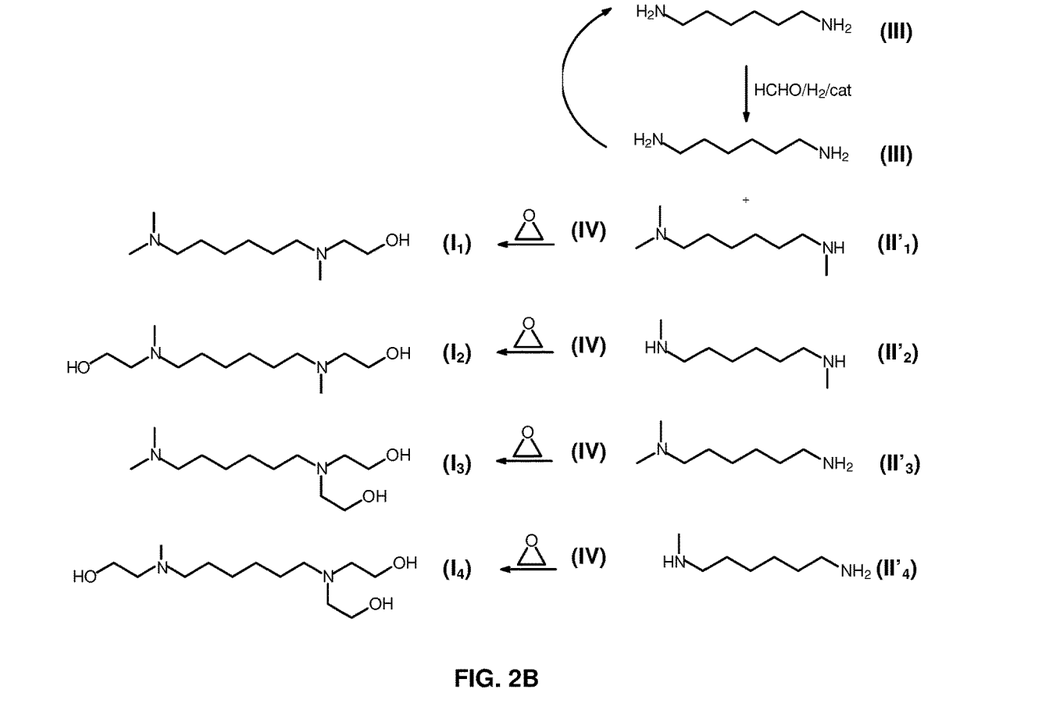

According to an alternative synthesis pathway from 1,6-hexanediamine, the ethoxylation and methylation steps can be reversed in relation to the pathway described above and illustrated in FIG. 2A. In this case, a first step of partial methylation of the 1,6-hexanediamine, by reaction with formaldehyde and hydrogen in the presence of a hydrogenation catalyst, leads to N-methyl-1,6-hexanediamine (formula ($II'_4$)) and/or to N,N-dimethyl-1,6-hexanediamine (formula ($II'_3$)) and/or to N,N'-dimethyl-1,6-hexanediamine (formula ($II'_2$)) and/or to N,N,N'-trimethyl-1,6-hexanediamine (formula ($II'_1$)). Then, in a second step, the primary and secondary amine functions are ethoxylated by reaction with ethylene oxide (formula (IV)). This variant of this first synthesis method is illustrated in FIG. 2B.

Method 2: Synthesis from 1,6-Hexanediol

A compound of general formula (I) can be synthesized from 1,6-hexanediol (formula (V)).

Figure 3:
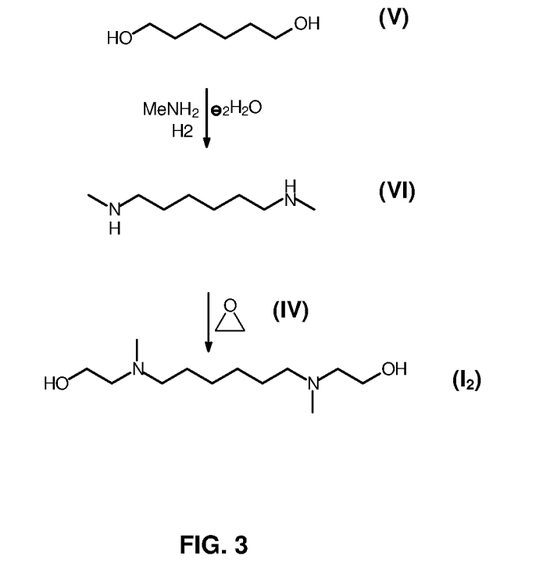
FIGS. 3 to 7 show pathways for the synthesis of N,N'-dimethyl-N-N'-di(2-hydroxyethyl)-1,6-hexanediamine (formula ($I_2$)), respectively from 1,6-hexanediol, adipaldehyde, dimethyl adipate or adipic acid in two steps, from dimethyl adipate or adipic acid in three steps.

FIG. 3 illustrates the synthesis of an example of a compound of general formula (I), N,N'-dimethyl-N,N'-di(2-hydroxyethyl)-1,6-hexanediamine of formula ($I_2$), from 1,6-hexanediol of formula (V).

The synthesis consists of the succession of two reaction steps: the condensation of 1,6-hexanediol with methylamine ($MeNH_2$) generally used in excess in the presence of hydrogen and of a suitable catalyst for leading to N,N'-dimethyl-1,6-hexanediamine (formula (VI)) which is subsequently converted to N,N'-dimethyl-N-N'-di(2-hydroxyethyl)-1,6-hexanediamine (formula ($I_2$)) through an ethoxylation reaction with ethylene oxide (formula (IV)).

Method 3: Synthesis from Adipaldehyde

A compound of general formula (I) can be synthesized from adipaldehyde.

Synthesis in 3 Reaction Steps

A compound of general formula (I) can be synthesized in three reaction steps from adipaldehyde (formula (VII)).

Figure 4:
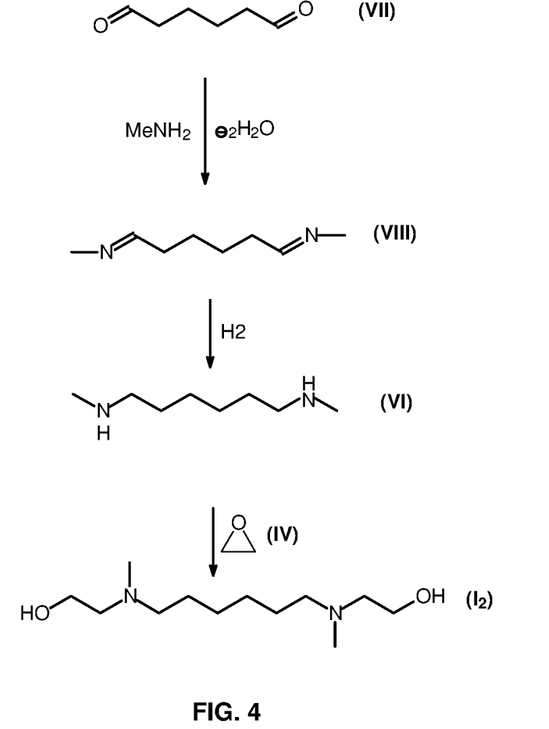

FIG. 4 illustrates the synthesis of an example of a compound of general formula (I), N,N'-dimethyl-N,N'-di(2-hydroxyethyl)-1,6-hexanediamine of formula ($I_2$), from adipaldehyde of formula (VII), according to a synthesis method in three reaction steps.

The synthesis consists of the succession of three reaction steps.

The first step consists in a condensation reaction of the adipaldehyde (formula (VII)) with methylamine leading to 1,6-bis(methylimino)-hexane (formula (VIII)).

A second reaction step consists in the reduction of the 1,6-bis(methylimino)-hexane (formula (VIII)) to N,N'-dimethyl-1,6-hexanediamine (formula (VI)).

A third reaction step consists in the ethoxylation of the N,N'-dimethyl-1,6-hexanediamine (formula (VI)) with ethylene oxide (formula (IV)) so as to form N,N'-dimethyl-N-N'-di(2-hydroxyethyl)-1,6-hexanediamine (formula ($I_2$)).

Synthesis in 1 Reaction Step

A compound of general formula (I) can be synthesized in a single step from adipaldehyde.

Figure 5:
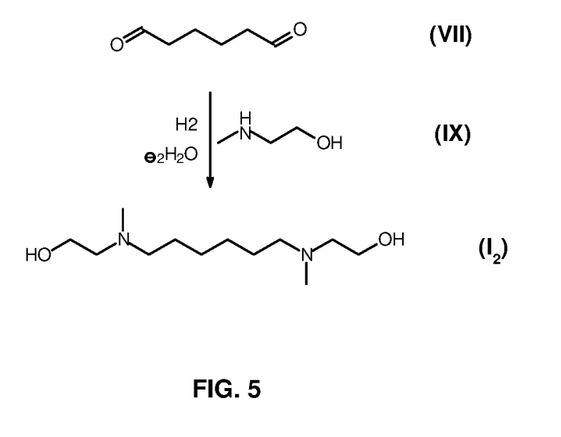

FIG. 5 illustrates the synthesis of an example of a compound of general formula (I), N,N'-dimethyl-N,N'-di(2-hydroxyethyl)-1,6-hexanediamine of formula ($I_2$), from adipaldehyde (formula (VII)), according to a synthesis method in a single step.

The synthesis consists in the condensation of the adipaldehyde (formula (VII)) with N-methyl-2-aminoethanol (formula (IX)) in the presence of hydrogen and of a suitable hydrogenation catalyst leading to N,N'-dimethyl-N-N'-di(2-hydroxyethyl)-1,6-hexane-diamine (formula ($I_2$)).

This transformation, also referred to as reductive amination, results from the succession of two reactions which are the condensation of a secondary amine with an aldehyde leading to an amine, then the hydrogenation thereof to a tertiary amine.

Method 4: Synthesis from Adipic Acid or From an Adipic Acid Diester

A compound of general formula (I) can be synthesized from adipic acid or from an adipic acid diester.

Synthesis in 2 Reaction Steps

A compound of general formula (I) can be synthesized in two reaction steps from adipic acid (formula (XI)) or from an adipic acid diester such as dimethyl adipate (formula X)).

Figure 6:
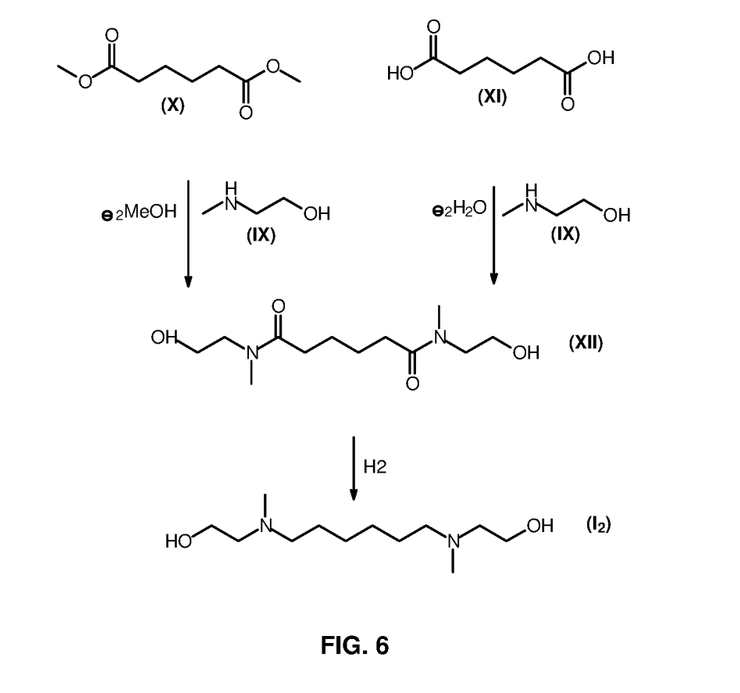

FIG. 6 illustrates the synthesis of an example of a compound of general formula (I), N,N'-dimethyl-N,N'-di(2-hydroxyethyl)-1,6-hexanediamine of formula ($I_2$), from adipic acid (formula (XI)) or from an adipic acid diester, such as dimethyl adipate (formula (x)), according to a synthesis method in two reaction steps.

A first step consists in the condensation reaction of N-methyl-2-aminoethanol (formula (IX)) with either adipic acid (formula (XI)) or an adipic acid diester such as, by way of non limitative example, dimethyl adipate (formula (x))or diethyl adipate. The condensation product obtained is a diamide, N,N'-dimethyl-N,N'-di(2-hydroxyethyl)-adipamide (formula (XII)).

The second step consists in the reduction of the amide functions of the N,N'-dimethyl-N,N'-di(2-hydroxyethyl)-adipamide (formula (XII)) to tertiary amine functions leading to N,N'-dimethyl-N,N'-di(2-hydroxyethyl)-1,6-hexanediamine (formula ($I_2$)).

This reduction can be carried out by any known means such as reduction by catalytic hydrogenation or the action of hydrides such as lithium and aluminium hydride.

Synthesis in 3 Reaction Steps

A compound of general formula (I) can be synthesized in three reaction steps from adipic acid (formula (XI)) or from an adipic acid diester such as dimethyl adipate (formula X)).

Figure 7:
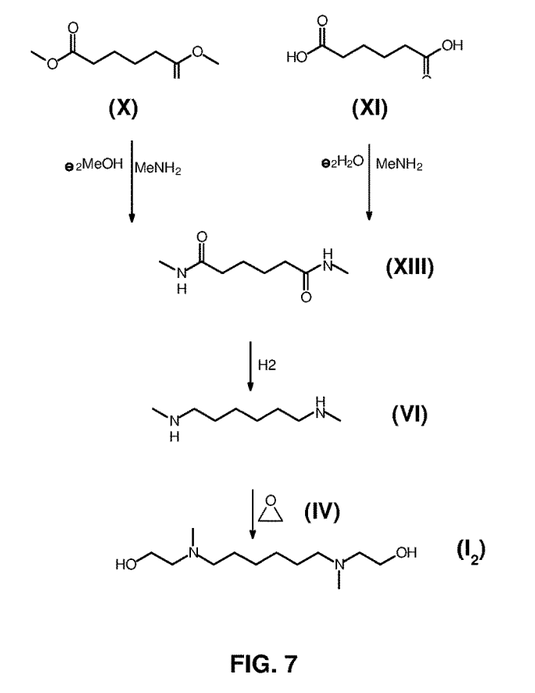

FIG. 7 illustrates the synthesis of an example of a compound of general formula (I), N,N'-dimethyl-N,N'-di(2-hydroxyethyl)-1,6-hexanediamine of formula ($I_2$), from adipic acid (formula (XI)) or from an adipic acid diester, such as dimethyl adipate (formula (x)), according to a synthesis method in three reaction steps.

A first step consists in the condensation of methylamine (MeNH2) with either adipic acid (formula (XI)) or an adipic acid diester such as, by way of non limitative example, dimethyl adipate (formula (x))or diethyl adipate. The condensation product obtained is a diamide: N,N'-dimethyl-N,N'-adipamide of formula (XIII).

A second step consists in the reduction of the amide functions of the N,N'-dimethyl-N,N'-adipamide of formula (XIII) to tertiary amine functions leading to N,N'-dimethyl-1,6-hexanediamine (formula (VI)). This reduction can be carried out by any known means such as reduction by catalytic hydrogenation or the action of hydrides such as lithium and aluminium hydride.

A third step consists in ethoxylating the secondary amine functions of the N,N'-dimethyl-1,6-hexanediamine (formula (VI)) with ethylene oxide (formula (IV)) leading to N,N'-dimethyl-N,N'-di(2-hydroxyethyl)-1,6-hexanediamine of formula ($I_2$).

Methods 1 to 4 described above allow to synthesize the compounds of general formula (I) from a family of precursors containing no halogen atom which will produce no hydrohalogenated acid. The reactions involved in these synthesis methods generate no salt to be separated and eliminated. Only co-products such as water and/or light alcohols are generated. Unlike the methods involving halogenated products and generating salts, these synthesis methods avoid the need for management and removal of a significant amount of salts, and they thus meet the current conditions relative to a green and sustainable chemistry, suited to an industrial-scale production.

Method 5: Synthesis from 1,6-Dihalohexane

Figure 8:
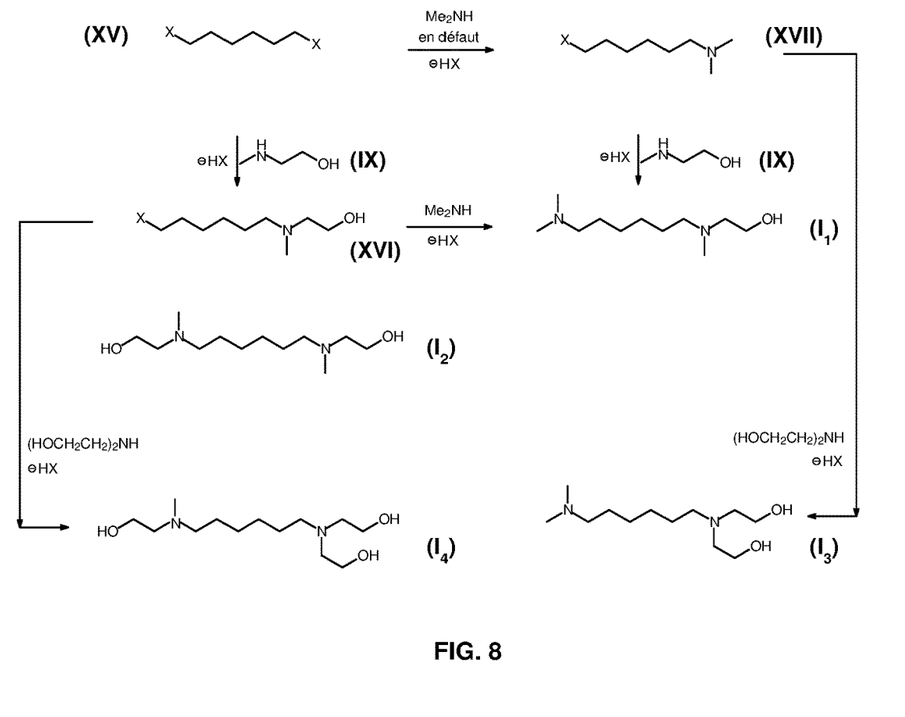
FIG. 8 shows a pathway for the synthesis of compounds of general formula (I) from 1,6-dihalohexane.

A compound of general formula (I) can be synthesized from 1,6-dihalohexane (formula (XV)). FIG. 8 illustrates such a method.

In formula (XV), X represents a chlorine, a bromine or an iodine atom. The 1,6-dihalohexane can thus be 1,6-dichlorohexane, 1,6-dibromohexane or 1,6-diiodohexane.

As represented in FIG. 8, the N,N'-dimethyl-N,N'-di(2-hydroxyethyl)-1,6-hexane-diamine of formula ($I_2$) can be obtained by condensation reaction of N-methyl-2-aminoethanol (formula (IX)) on a 1,6-dihalohexane of formula (XV). This reaction can also lead to N-methyl-N-(2-hydroxyethyl)-1-halo-6-hexylamine (formula (XVI)).

This method can also be applied to the synthesis of N,N,N'-trimethyl-N'-(2-hydroxyethyl)-1,6-hexanediamine (formula ($I_1$)) or N,N-dimethyl-N'-N'-di(2-hydroxyethyl)-1,6-hexanediamine(formula ($I_3$)) or N-methyl-N-N'-N'-tri(2-hydroxyethyl)-1,6-hexane-diamine (formula ($I_4$)) by conducting the reaction using, in an appropriate manner, with N-methyl-2-aminoethanol (formula (IX)), dimethylamine ($Me_2NH$) or diethanolamine ($HOCH_2CH_2)_2NH$, successively or simultaneously. Another pathway consists in conducting the condensation reaction using in an appropriate manner, instead of N-methyl-2-aminoethanol (formula (IX)) alone, dimethylamine ($Me_2NH$) and diethanolamine ($HOCH_2CH_2)_2NH$, successively or simultaneously. The compound of formula (XVI) and N,N-dimethyl-1-halo-6-hexylamine (formula (XVII)) can be formed during these reactions so as to lead to N,N,N'-trimethyl-N'-(2-hydroxyethyl)-1,6-hexanediamine (formula ($I_1$)), N,N-dimethyl-N'-N'-di(2-hydroxyethyl)-1,6-hexanediamine (formula ($I_3$)) or N-methyl-N-N'-N'-tri(2-hydroxyethyl)-1,6-hexanediamine (formula ($I_4$)).

Nature of the Gaseous Effluents

According to the invention, the absorbent solutions can be used for deacidizing the following gaseous effluents: natural gas, syngas, combustion fumes, refinery gas, acid gas from an amine plant, Claus tail gas, biomass fermentation gas, cement plant gas and incinerator fumes. These gaseous effluents contain one or more of the following acid compounds: $CO_2$, $H_2S$, mercaptans (for example methylmercaptan ($CH_3SH$), ethylmercaptan ($CH_3CH_2SH$), propylmercaptan ($CH_3CH_2CH_2SH$)), COS, $CS_2$, $SO_2$.

Combustion fumes are produced notably by the combustion of hydrocarbons, biogas, coal in a boiler or for a combustion gas turbine, for example in order to produce electricity. By way of illustration, a deacidizing method according to the invention can be implemented for absorbing at least 70%, preferably at least 80% or even at least 90% of the $CO_2$ contained in combustion fumes. These fumes generally have a temperature ranging between 20° C. and 60° C., a pressure ranging between 1 and 5 bar, and they can comprise between 50% and 80% nitrogen, between 5% and 40% carbon dioxide, between 1% and 20% oxygen, and some impurities such as SOx and NOx if they have not been removed upstream from the deacidizing process. In particular, the deacidizing method according to the invention is particularly well suited for absorbing the $CO_2$ contained in combustion fumes having a low $CO_2$ partial pressure, for example a $CO_2$ partial pressure below 200 mbar.

The deacidizing method according to the invention can be implemented for deacidizing a syngas. Syngas contains carbon monoxide CO, hydrogen $H_2$ (generally with a $H_2/CO$ ratio of 2), water vapour (generally at saturation at the wash temperature) and carbon dioxide $CO_2$ (of the order of 10%).

The pressure generally ranges between 20 and 30 bar, but it can reach up to 70 bar. It can also comprise sulfur-containing ($H_2S$, COS, etc.), nitrogen-containing ($NH_3$, HCN) and halogenated impurities.

The deacidizing method according to the invention can be implemented for deacidizing a natural gas. Natural gas predominantly consists of gaseous hydrocarbons, but it can contain some of the following acid compounds: $CO_2$, $H_2S$, mercaptans, COS, $CS_2$. The proportion of these acid compounds is very variable and it can reach up to 70 vol. % for $CO_2$ and up to 40 vol. % for $H_2S$. The temperature of the natural gas can range between 20° C. and 100° C. The pressure of the natural gas to be treated can range between 10 and 200 bar. The invention can be implemented in order to reach specifications generally imposed on deacidized gas, which are less than 2% $CO_2$, or even less than 50 ppm $CO_2$ so as to subsequently carry out liquefaction of the natural gas, less than 4 ppm $H_2S$, and less than 50 ppm or even less than 10 ppm by volume of total sulfur.

Method of Removing Acid Compounds from a Gaseous Effluent

Figure 1:
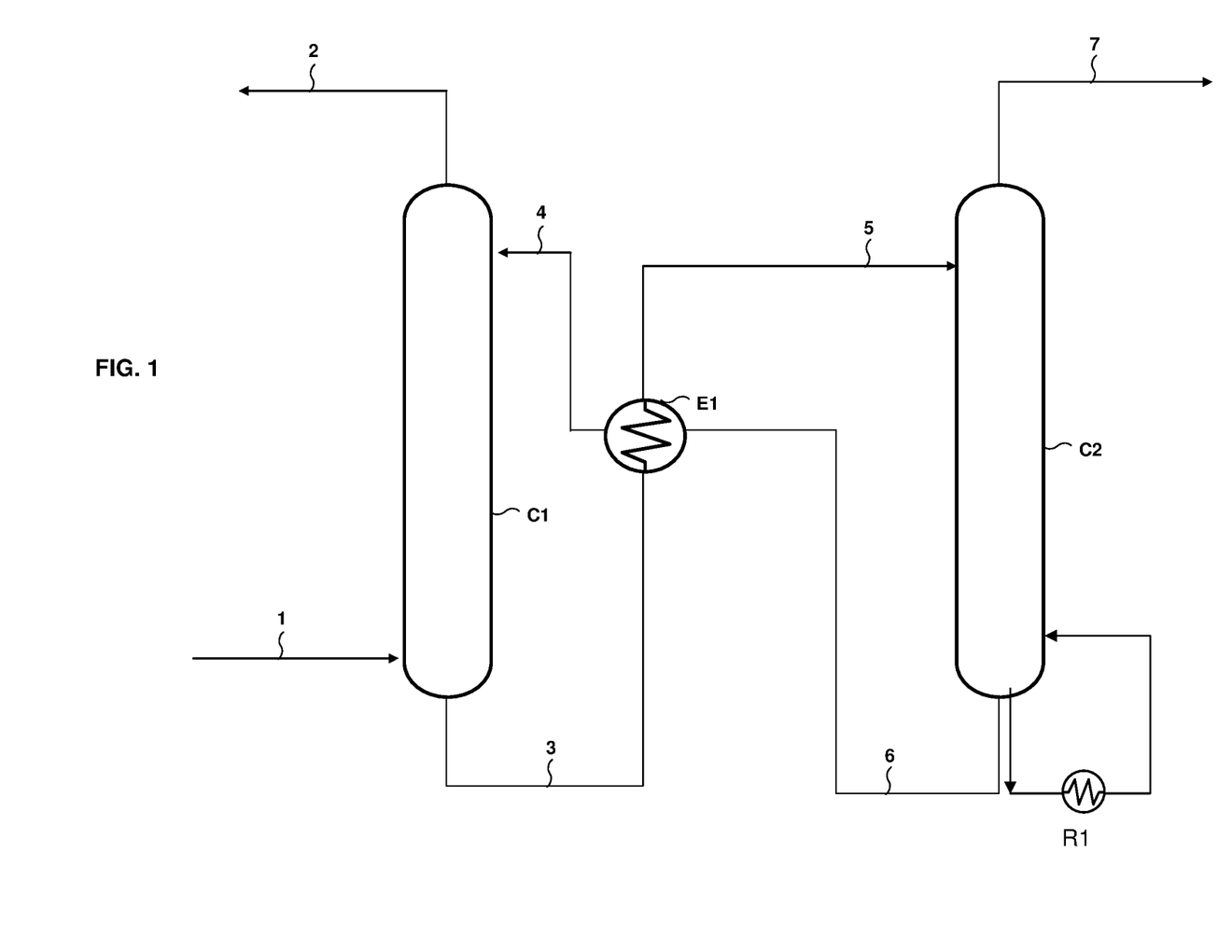
FIG. 1 is a block diagram of the implementation of an acid gas treating method.

Using an aqueous solution comprising at least one nitrogen compound of general formula (I) for deacidizing a gaseous effluent is schematically done by carrying out an absorption step followed by a regeneration step, as shown in FIG. 1 for example.

With reference to FIG. 1, the plant for deacidizing a gaseous effluent according to the invention comprises an absorption column C1 provided with means for contacting the gas and the liquid, for example a random packing, a structured packing or trays. The gaseous effluent to be treated is fed through a line 1 opening into the bottom of column C1. A line 4 allows the absorbent solution to be fed to the top of column C1. A line 2 allows the treated (deacidized) gas to be discharged and a line 3 allows the absorbent solution enriched in acid compounds following absorption to be sent to a regeneration column C2. This regeneration column C2 is provided with gas-liquid contacting internals, for example trays, random or structured packings. The bottom of column C2 is equipped with a reboiler R1 that provides the heat required for regeneration by vaporizing a fraction of the absorbent solution. The acid compound-enriched solution is fed to the top of regeneration column C2 through a line 5. A line 7 allows to discharge at the top of column C2 the gas enriched in acid compounds released upon regeneration, and a line 6 arranged in the bottom of column C2 allows the regenerated absorbent solution to be sent to absorption column C1. A heat exchanger E1 allows the heat of the regenerated absorbent solution from column C2 to be recovered so as to heat the acid compound-enriched absorbent solution leaving absorption column C1.

The absorption step consists in contacting the gaseous effluent delivered through line 1 with the absorbent solution delivered through line 4. Upon contact, the amine functions of the molecules of the absorbent solution react with the acid compounds contained in the effluent so as to obtain an acid compound-depleted gaseous effluent that is discharged through line 2 at the top of column C1 and an acid compound-enriched absorbent solution that is discharged through line 3 in the bottom of column C1 to be regenerated.

The acid compound absorption step can be carried out at a pressure in column C1 ranging between 1 and 200 bar, preferably between 20 and 100 bar for natural gas treatment, preferably between 1 and 3 bar for industrial fumes treatment, and at a temperature in column C1 ranging between 20° C. and 100° C., preferably between 30° C. and 90° C., or even between 30° C. and 60° C.

The regeneration step notably consists in heating and optionally in expanding the acid compound-enriched absorbent solution so as to release the acid compounds in gas form. The acid compound-enriched absorbent solution leaving column C1 is fed to heat exchanger E1 where it is heated by the stream circulating in line 6 and coming from regeneration column C2. The heated solution at the outlet of E1 is fed to regeneration column C2 through line 5.

In regeneration column C2, under the effect of contacting the absorbent solution flowing in through line 5 with the vapour produced by the reboiler, the acid compounds are released in gas form and discharged at the top of column C2 through line 7. The regenerated absorbent solution, i.e. depleted in acid compounds, is discharged through line 6 and cooled in E1, then recycled to absorption column C1 through line 4.

The regeneration step can be carried out by thermal regeneration, optionally complemented by one or more expansion steps. For example, the acid compound-enriched absorbent solution discharged through line 3 can be sent to a first flash drum (not shown) prior to being sent to heat exchanger E1. In the case of natural gas, expansion allows to obtain a gas discharged at the top of the drum that contains the major part of the aliphatic hydrocarbons co-absorbed by the absorbent solution. This gas can be optionally washed by a fraction of the regenerated absorbent solution and the gas thus obtained can be used as fuel gas. The flash drum preferably operates at a pressure lower than in absorption column C1 and higher than in regeneration column C2. This pressure is generally determined by the conditions of use of the fuel gas, and it is typically of the order of 5 to 15 bar. The flash drum operates at a temperature substantially identical to the temperature of the absorbent solution obtained in the bottom of absorption column C1.

Regeneration can be carried out at a pressure in column C2 ranging between 1 and 5 bar, or even up to 10 bar, and at a temperature in column C2 ranging between 100° C. and 180° C., preferably between 110° C. and 170° C., more preferably between 120° C. and 140° C. Preferably, the regeneration temperature in column C2 ranges between 155° C. and 180° C. in cases where the acid gases are intended to be reinjected. Preferably, the regeneration temperature in column C2 ranges between 115° C. and 130° C. in cases where the acid gas is sent to the atmosphere or to a downstream treating process such as a Claus process or a tail gas treating process.

EXAMPLES

The examples below illustrate by way of non limitative example the synthesis of nitrogen compounds of general formula (I), and some performances of these compounds when used in aqueous solution for removing acid compounds such as $CO_2$ or $H_2S$ contained in a gaseous effluent by contacting the gaseous effluent with the solution.

Example 1: Synthesis of N,N'-dimethyl-N,N'-di(2-hydroxyethyl)-1,6-hexanediamine

The synthesis of N,N'-dimethyl-N,N'-di(2-hydroxyethyl)-1,6-hexanediamine of formula ($I_2$) is carried out on a laboratory scale.

160.5 g (1.035 mol) of 1,6-dichlorohexane are reacted with 262.5 g (3.50 mol) of N-methylaminoethanol for 3 hours at 100° C. After return to ambient temperature, the medium is neutralized with a solution of 83.6 g soda in 240.0 g water, then filtration of the salt formed is performed. After evaporation of the water and of the excess N-methylaminoethanol, 158.1 g of a product whose $^{13}$C NMR spectrum summarized hereafter matches that of N,N'-dimethyl-N,N'-di(2-hydroxyethyl)-1,6-hexanediamine are isolated by distillation under reduced pressure.

26.2 ppm: HO—$CH_2$—$CH_2$—N($CH_3$)—$CH_2$—$CH_2$—$CH_2$—$CH_2$—$CH_2$—$CH_2$—N($CH_3$)—$CH_2$—$CH_2$—OH
26.5 ppm: HO—$CH_2$—$CH_2$—N($CH_3$)—$CH_2$—$CH_2$—$CH_2$—$CH_2$—$CH_2$—$CH_2$—N($CH_3$)—$CH_2$—$CH_2$—OH
41.3 ppm: HO—$CH_2$—$CH_2$—N($CH_3$)—$CH_2$—$CH_2$—$CH_2$—$CH_2$—$CH_2$—$CH_2$—N($CH_3$)—$CH_2$—$CH_2$—OH
57.2 ppm: HO—$CH_2$—$CH_2$—N($CH_3$)—$CH_2$—$CH_2$—$CH_2$—$CH_2$—$CH_2$—$CH_2$—N($CH_3$)—$CH_2$—$CH_2$—OH
58.0 ppm: HO—$CH_2$—$CH_2$—N($CH_3$)—$CH_2$—$CH_2$—$CH_2$—$CH_2$—$CH_2$—$CH_2$—N($CH_3$)—$CH_2$—$CH_2$—OH
58.5 ppm: HO—$CH_2$—$CH_2$—N($CH_3$)—$CH_2$—$CH_2$—$CH_2$—$CH_2$—$CH_2$—$CH_2$—N($CH_3$)—$CH_2$—$CH_2$—OH.

Example 2: Synthesis of a mixture of N,N'-dimethyl-N,N'-di(2-hydroxyethyl)-1,6-hexanediamine and of N,N,N'-trimethyl-N'-(2-hydroxyethyl)-1,6-hexanediamine 155.0 g (1.0 mol) of 1,6-dichlorohexane are reacted in an autoclave with 300.0 g (4.0 mol) of N-methylaminoethanol and 96.75 g of a 40% dimethylamine aqueous solution for 4 hours at 100° C. After return to ambient temperature, the medium is neutralized with a solution of 80.0 g soda in 80.0 g water, then filtration of the salt formed is performed. After evaporation of the water and of the excess dimethylamine and N-methylaminoethanol, 181.5 g of a product containing 73% N,N'-dimethyl-N,N'-di(2-hydroxyethyl)-1,6-hexanediamine (formula ($I_2$)) and 27% N,N,N'-trimethyl-N'-(2-hydroxyethyl)-1,6-hexanediamine (formula ($I_1$)) are isolated by distillation under reduced pressure.

Example 3: $CO_2$ Absorption Rate of an Amine Formulation for a Selective Absorption Method Comparative $CO_2$ absorption tests are carried out with different absorbent solutions:
- an absorbent solution comprising a mixture of 20 wt. % N,N'-dimethyl-N,N'-di(2-hydroxyethyl)-1,6-hexanediamine, 30 wt. % N-methyldiethanolamine (MDEA) and 50 wt. % water according to the invention,
- an aqueous MDEA solution with 47 wt. % MDEA, which is a reference absorbent solution for selective removal in gas treatment,
- an aqueous solution of 1,2-bis-(pyrrolidinylethoxy)-ethane with 50 wt. % 1,2-bis-(pyrrolidinylethoxy)-ethane, which is a diaminoether with two tertiary amine functions according to the general formula of patent U.S. Pat. No. 4,405,582 but has no alcohol function and does not fall within general formula (I),
- an aqueous solution of 1,2-bis-(tertiobutylaminoethoxy)-ethane with 40 wt. % 1,2-bis-(tertiobutylaminoethoxy)-ethane, which is a diaminoether with two secondary functions having severe steric hindrance of the nitrogen atoms according to the general formula of patent U.S. Pat. NO. 4,405,583, with no alcohol function and which does not fall within general formula (I),
- an aqueous solution of N,N,N',N'-tetramethyl-1,6-hexanediamine (TMHDA) with 50 wt. % TMHDA, which is a tertiary diamine disclosed in patent FR-2,934,172, but which has no alcohol function and does not fall within general formula (I).

For each test, the $CO_2$ flow absorbed by the aqueous absorbent solution is measured in a closed reactor of Lewis cell type. 200 g solution are fed into the closed reactor at a controlled temperature of 50° C. Four successive $CO_2$ injections are carried out from 100 to 200 mbar in the vapour phase of the 200 $cm^3$-volume reactor. The gas phase and the liquid phase are stirred at 100 rpm and entirely characterized from the hydrodynamic point of view. For each injection, the $CO_2$ absorption rate is measured through pressure variation in the gas phase. A global transfer coefficient Kg is thus determined using a mean of the results obtained for the four injections.

The results obtained are shown in Table 1 hereafter in relative absorption rate by comparison with the reference aqueous absorbent solution comprising 47 wt. % MDEA, this relative absorption rate being defined by the ratio of the global transfer coefficient of the absorbent solution tested to the global transfer coefficient of the reference absorbent solution (with MDEA).

TABLE 1

| Compounds | Total amine concentration (wt. %) | $CO_2$ relative absorption rate at 50° C. |
|---|---|---|
| MDEA | 47 | 1.00 |
| 1,2-bis-(pyrrolidinylethoxy)-ethane (according to U.S. Pat. No. 4,405,582) | 50 | 1.43 |
| 1,2-bis-(tertiobutylaminoethoxy)-ethane (according to U.S. Pat. No. 4,405,583) | 40 | 1.74 |
| TMHDA (according to FR-2,934,172) | 50 | 2.72 |
| 20 wt. % N,N'-dimethyl-N-N'-di(2-hydroxyethyl)-1,6-hexanediamine + 30 wt. % MDEA according to the invention | 50 | 0.94 |

The results show, under these test conditions, a slower rate of absorption of $CO_2$ by the absorbent solution according to the invention compared to the reference formulation with MDEA and compared to the absorbent solutions with some molecules of the prior art. It therefore appears that the exemplified compound according to the invention surprisingly is of particular and improved interest in the case of selective deacidizing of a gaseous effluent where the $CO_2$ absorption kinetics is to be limited.

Example 4: $H_2S$ Absorption Capacity of a N,N'-dimethyl-N,N'-di(2-hydroxyethyl)-1,6-hexanediamine Formulation for an Acid Gas Treating Method The $H_2S$ absorption capacity performances at 40° C. of an aqueous solution of N,N'-dimethyl-N,N'-di(2-hydroxyethyl)-1,6-hexanediamine according to the invention, containing 20 wt. % N,N'-dimethyl-N,N'-di(2-hydroxyethyl)-1,6-hexanediamine and 30 wt. % MDEA, are compared with those of an MDEA aqueous solution containing 50 wt. % MDEA, which is a reference absorbent solution for deacidizing $H_2S$-containing gas.

An absorption test is carried out at 40° C. on aqueous amine solutions in a thermostat-controlled equilibrium cell. This test consists in injecting into the equilibrium cell, previously filled with degassed aqueous amine solution, a known amount of acid gas, $H_2S$ in this example, then in waiting for the equilibrium state to be reached. The amounts of acid gas absorbed in the aqueous amine solution are then deduced from the temperature and pressure measurements by means of material and volume balances. The solubilities are conventionally represented in form of $H_2S$ partial pressures (in bar) as a function of the $H_2S$ loading (in mol of $H_2S$/kg absorbent solution and in mol of $H_2S$/mol of amine).

In the case of deacidizing in natural gas treatment, the $H_2S$ partial pressures encountered in acid gases typically range between 0.1 and 1 bar at a temperature of 40° C. By way of example, in this industrial range, Table 2 hereafter compares the $H_2S$ loadings obtained at 40° C. for various $H_2S$ partial pressures between the 50 wt. % MDEA absorbent solution and the absorbent solution of N,N'-dimethyl-N,N'-di(2-hydroxyethyl)-1,6-hexanediamine according to the invention, containing 20 wt. % N,N'-dimethyl-N,N'-di(2-hydroxyethyl)-1,6-hexanediamine and 30 wt. % MDEA.

TABLE 2

| $H_2S$ partial pressure (bar) | 20 wt. % N,N'-dimethyl-N-N'-di(2-hydroxyethyl)-1,6-hexanediamine + 30 wt. % MDEA according to the invention at 40° C. | | 50 wt. % MDEA aqueous solution at 40° C. | |
|---|---|---|---|---|
| | $H_2S$ loading (mol/mol amine) | $H_2S$ loading (mol/kg) | $H_2S$ loading (mol/mol amine) | $H_2S$ loading (mol/kg) |
| 0.10 | 0.41 | 1.39 | 0.21 | 0.88 |
| 1 | 0.99 | 3.34 | 0.69 | 2.95 |

At 40° C., whatever the $H_2S$ partial pressure, the absorption capacity of the N,N'-dimethyl-N,N'-di(2-hydroxyethyl)-1,6-hexanediamine aqueous solution according to the invention is higher than that of the MDEA solution.

At a $H_2S$ partial pressure of 0.10 bar, the difference between the $H_2S$ loadings of the two absorbent solutions is 0.51 mol/kg, with an absorption capacity for the N,N'-dimethyl-N,N'-di(2-hydroxyethyl)-1,6-hexanediamine absorbent solution increased by 58% in relation to the reference MDEA absorbent solution.

At a $H_2S$ partial pressure of 1 bar, the $H_2S$ loading increase for the N,N'-dimethyl-N,N'-di(2-hydroxyethyl)-1,6-hexanediamine absorbent solution still is 13% in relation to the reference MDEA absorbent solution.

It can thus be observed that the N,N'-dimethyl-N,N'-di(2-hydroxyethyl)-1,6-hexanediamine aqueous solution according to the invention has a higher $H_2S$ absorption capacity than the reference 50 wt. % MDEA aqueous solution at 40° C., in the $H_2S$ partial pressure range between 0.1 and 1 bar corresponding to a partial pressure range representative of usual industrial conditions.

It thus appears that this exemplified molecule according to the invention allows to reduce the absorbent solution flow rates required in $H_2S$-containing gas deacidizing applications compared to the reference MDEA absorbent solution.

$CO_2$ absorption being slower in a N,N'-dimethyl-N,N'-di(2-hydroxyethyl)-1,6-hexane-diamine aqueous solution according to the invention than in a MDEA aqueous solution (see Example 3 above) and the acid gas, notably $H_2S$, absorption capacity being equivalent or higher with the N,N'-dimethyl-N,N'-di(2-hydroxyethyl)-1,6-hexane-diamine absorbent solution in relation to a MDEA aqueous solution as illustrated in the present example, it appears that this exemplified molecule according to the invention allows to reduce the absorbent solution flow rates required in selective deacidizing applications ($H_2S$ over $CO_2$) for absorbing a given flow of $H_2S$ while reducing the flow of co-absorbed $CO_2$ in relation to the reference MDEA absorbent solution.

Example 5: $CO_2$ Absorption Capacity of a N,N'-dimethyl-N,N'-di(2-hydroxyethyl)-1,6-hexanediamine Formulation for a Total Deacidizinq Application in Acid Gas Treatment The $CO_2$ absorption capacity performances at 40° C. of a N,N'-dimethyl-N,N'-di(2-hydroxyethyl)-1,6-hexanediamine aqueous solution according to the invention, containing 42 wt. % N,N'-dimethyl-N,N'-di(2-hydroxyethyl)-1,6-hexanediamine and 5.3 wt. % piperazine, are compared with those of an MDEA aqueous solution containing 39 wt. % MDEA and 6.7 wt. % piperazine, which is a reference absorbent solution for a total deacidizing application.

An absorption test is carried out at 40° C. according to the operating mode described in the previous examples, the acid gas being $CO_2$ instead of $H_2S$.

In the case of deacidizing in natural gas treatment, the $CO_2$ partial pressures encountered in acid gases typically range between 0.1 and 1 bar at a temperature of 40° C. By way of example, in this industrial range, Table 3 below compares the $CO_2$ loadings obtained at 40° C. for various $CO_2$ partial pressures between the 39 wt. % MDEA and 6.7 wt. % piperazine absorbent solution and the 42 wt. % N,N'-dimethyl-N,N'-di(2-hydroxyethyl)-1,6-hexanediamine and 5.3 wt. % piperazine absorbent solution.

TABLE 3

| $CO_2$ partial pressure (bar) | 42 wt. % N,N'-dimethyl-N-N'-di(2-hydroxyethyl)-1,6-hexanediamine and 5.3 wt. % piperazine aqueous solution at 40° C. | | 39 wt. % MDEA and 6.7 wt. % piperazine aqueous solution at 40° C. | |
|---|---|---|---|---|
| | $CO_2$ loading (mol/mol amine) | $CO_2$ loading (mol/kg) | $CO_2$ loading (mol/mol amine) | $CO_2$ loading (mol/kg) |
| 0.10 | 0.88 | 2.14 | 0.39 | 1.60 |
| 1.00 | 1.48 | 3.58 | 0.73 | 2.96 |

At 40° C., whatever the $CO_2$ partial pressure, the absorption capacity of the N,N'-dimethyl-N,N'-di(2-hydroxyethyl)-1,6-hexanediamine aqueous solution activated with 5.3 wt. % piperazine according to the invention is higher than that of the MDEA solution activated with 6.7 wt. % piperazine.

At a $CO_2$ partial pressure of 0.10 bar, the difference between the $CO_2$ loadings of the two absorbent solutions is 0.54 mol/kg with an absorption capacity for the N,N'-dimethyl-N,N'-di(2-hydroxyethyl)-1,6-hexanediamine absorbent solution increased by 34% in relation to the reference activated MDEA absorbent solution.

At a $CO_2$ partial pressure of 1 bar, the $CO_2$ loading increase for the activated N,N'-dimethyl-N,N'-di(2-hydroxyethyl)-1,6-hexanediamine absorbent solution still is 21% in relation to the reference activated MDEA absorbent solution.

It can thus be observed that the 42 wt. % N,N'-dimethyl-N,N'-di(2-hydroxyethyl)-1,6-hexanediamine aqueous solution activated with 5.3 wt. % piperazine has a higher $CO_2$ absorption capacity at 40° C. than the reference 39 wt. % MDEA aqueous solution activated with 6.7 wt. % piperazine, in the $CO_2$ partial pressure range between 0.1 and 1 bar corresponding to a partial pressure range representative of usual industrial conditions.

It thus appears that this exemplified molecule according to the invention allows to reduce the absorbent solution flow rates required in $CO_2$-containing gas deacidizing applications compared to the reference activated MDEA absorbent solution.

The invention claimed is:

1. A method of removing acid compounds contained in a gaseous effluent, wherein an acid compound absorption step is carried out by contacting the gaseous effluent with an absorbent solution comprising:
water, and
at least one nitrogen compound of formula (I) as follows:

wherein:
radicals $R_1$, $R_2$, $R_3$ are each selected independently from a methyl radical and a
hydroxyethyl radical, provided that at least one radical $R_1$, $R_2$, $R_3$ is a methyl radical.

2. A method as claimed in claim 1, wherein the acid compound absorption step is carried out at a pressure ranging between 1 bar and 200 bar, and at a temperature ranging between 20° C. and 100° C.

3. A method as claimed in claim 1, wherein an absorbent solution laden with acid compounds is obtained after the absorption step and at least one step of regenerating said acid compound-laden absorbent solution is performed at a pressure ranging between 1 bar and 10 bar, and at a temperature ranging between 100° C. and 180° C.

4. A method as claimed in claim 1, wherein the gaseous effluent is selected among natural gas, syngases, combustion fumes, refinery gas, acid gas from an amine plant, Claus tail gas, biomass fermentation gas, cement plant gas and incinerator fumes.

5. A method as claimed in claim 1, implemented for selectively removing the $H_2S$ over the $CO_2$ from a gaseous effluent comprising $H_2S$ and $CO_2$, preferably natural gas.

6. A method as claimed in claim 1, wherein said at least one nitrogen compound of formula (I) is selected from the following compounds:
N,N,N'-trimethyl-N'-(2-hydroxyethyl)-1,6-hexanediamine of formula ($I_1$) as follows:

N,N'-dimethyl-N,N'-di(2-hydroxyethyl)-1,6-hexanediamine of formula ($I_2$):

N,N-dimethyl-N',N'-di(2-hydroxyethyl)-1,6-hexanediamine of formula ($I_3$):

N-methyl-N,N',N'-tri(2-hydroxyethyl)-1,6-hexanediamine of formula ($I_4$):

7. A method as claimed in claim 6, wherein said compound is N,N,N'-trimethyl-N'-(2-hydroxyethyl)-1,6-hexanediamine of formula ($I_1$) or N,N'-dimethyl-N,N'-di(2-hydroxyethyl)-1,6-hexanediamine of formula ($I_2$).

8. A method as claimed in claim 1, wherein the absorbent solution comprises between 5 wt. % and 95 wt. % of said nitrogen compound of formula (I) and between 5 wt. % and 95 wt. % of water.

9. A method as claimed in claim 1, wherein the absorbent solution comprises between 10 wt. % and 90 wt. % of said nitrogen compound of formula (I) and between 10 wt. % and 90 wt. % of water.

10. A method as claimed in claim 1, wherein the absorbent solution comprises between 20 wt. % and 50 wt. % of said nitrogen compound of formula (I) and between 50 wt. % and 80 wt. % of water.

11. A method as claimed in claim 1, wherein the absorbent solution further comprises between 5 wt. % and 95 wt. % of at least one additional amine, said additional amine being either a tertiary amine or a secondary amine having two secondary carbons at nitrogen alpha position or at least one tertiary carbon at nitrogen alpha position.

12. A method as claimed in claim 11, wherein said additional amine is a tertiary amine selected from the group consisting of:
N-methyldiethanolamine,
triethanolamine,
diethylmonoethanolamine,
dimethylmonoethanolamine, and
ethyldiethanolamine.

13. A method as claimed in claim 1, wherein the absorbent solution further comprises a non-zero amount, less than 30 wt. %, of at least one primary or secondary amine.

14. A method as claimed in claim 13, said primary or secondary amine is selected from the group consisting of:
monoethanolamine,
diethanolamine,
N-butylethanolamine,
aminoethylethanolamine,
diglycolamine,
piperazine,
1-methylpiperazine,
2-methylpiperazine,
homopiperazine,
N-(2-hydroxyethyl)piperazine,
N-(2-aminoethyl)piperazine,
morpholine,
3-(methylamino)propylamine,
1,6-hexanediamine,
N,N-dimethyl-1,6-hexanediamine,
N,N'-dimethyl-1,6-hexanediamine,
N-methyl-1,6-hexanediamine, and
N,N',N'-trimethyl-1,6-hexanediamine.

15. A method as claimed in claim 1, wherein the absorbent solution further comprises at least one physical solvent selected from the group consisting of methanol, ethanol, 2-ethoxyethanol, triethylene glycol dimethyl ether, tetraethylene glycol dimethyl ether, pentaethylene glycol dimethyl ether, hexaethylene glycol dimethyl ether, heptaethylene glycol dimethyl ether, octaethylene glycol dimethyl ether, diethylene glycol butoxyacetate, glycerol triacetate, sulfolane, N-methyl-pyrrolidone, N-methylmorpholin-3-one, N,N-dimethylformamide, N-formylmorpholine, N,N-dimethyl-imidazolidin-2-one, N-methylimidazole, ethylene glycol, diethylene glycol, triethylene glycol, thiodiglycol, propylene carbonate and tributyl phosphate.

* * * * *